United States Patent [19]

Huhn et al.

[11] 3,989,837
[45] *Nov. 2, 1976

[54] PHARMACEUTICAL COMPOSITIONS

[75] Inventors: Magda Huhn; László Tardos; Eva Somfai; Gábor Resorszki; Vera Kovacs née Mindler; Maria Palffy nee Oswald, all of Budapest, Hungary

[73] Assignee: Chinoin Gyogyszer-es Vegyeszeti Termekek Gyara RT, Budapest, Hungary

[*] Notice: The portion of the term of this patent subsequent to May 27, 1992, has been disclaimed.

[22] Filed: Apr. 4, 1975

[21] Appl. No.: 565,115

Related U.S. Application Data

[63] Continuation-in-part of Ser. No. 387,964, Aug. 13, 1973, Pat. No. 3,886,279.

[30] Foreign Application Priority Data

Aug. 24, 1972 Hungary.............................. CI1268

[52] U.S. Cl................................ 424/274; 424/263; 424/270
[51] Int. Cl.² .................. A61K 31/40; A61K 31/44; A61K 31/425
[58] Field of Search..................... 424/274, 263, 270

[56] References Cited
UNITED STATES PATENTS 3,488,731  1/1970  Sletzenger.................... 260/326.13
3,886,279  5/1975  Huhn et al........................ 424/274

Primary Examiner—Stanley J. Friedman
Attorney, Agent, or Firm—Karl F. Ross; Herbert Dubno

[57] ABSTRACT

An anti-inflammatory analgesic pharmaceutical composition comprising as active ingredient a compound of the formula I

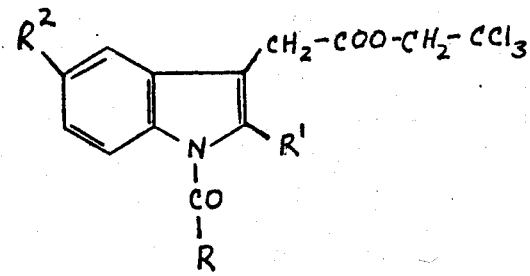

wherein
R is a phenyl, chlorophenyl, naphthyl, pyrole, furane, furazole, thiazole, thiadiazole or pyridine group;
R¹ is hydrogen or alkyl having 1 to 7 carbon atoms;
R² is hydrogen, alkyl having 1 to 7 carbon atoms, alkoxy having 1 to 7 carbon atoms or dialkylamino having 1 to 7 carbon atoms per alkyl group in admixture with a pharmaceutical carrier.

2 Claims, No Drawings

PHARMACEUTICAL COMPOSITIONS

This application is a continuation-in-part of copending application Ser. No. 387,964 filed Aug. 13, 1973, now U.S. Pat. No. 3,886,279 issued May 27, 1975.

This invention relates to pharmaceutical compositions having anti-inflammatory and analgesic properties. More particularly the present invention is directed to pharmaceutical compositions containing N-acylated-iudole-3-carboxylic acid esters and a process for the preparation of such compositions.

The active ingredients of the invention compound correspond to the formula (1)

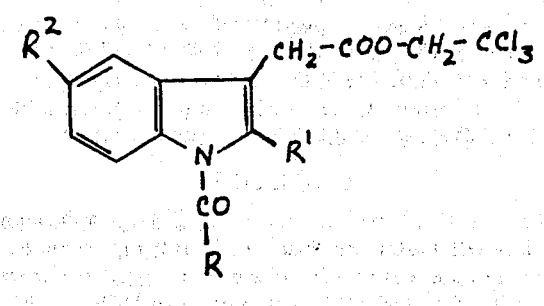

wherein
- R is a substituted or unsubstituted aryl group or a substituted or unsubstituted heterocyclic group containing one or more oxygen, sulphur or nitrogen heteroatoms;
- $R^1$ is hydrogen or alkyl; and
- $R^2$ is hydrogen, alkyl, alkoxy or dislkylamino.

The pharmaceutical compositions of the present invention contain as active ingredient a compound of the above formula in admixture with inert solid or liquid pharmaceutical carriers and optionally further additives.

In the formula, R is preferably for a phenyl, naphthyl, pyrrole, furane, furazole, thiazole, thiadiazole, or pyridine ring which may be unsubstituted with halogen and/or nitro groups.

The term "alkyl group" as used in the specification means straight or branched-chain groups having 1–7 preferably 1–4 carbon atoms (e.g. methyl, ethyl, n-propyl, isobutyl etc.). The "alkoxy groups" may also be straight or branched chain and contain 1–7, preferably 1–4 carbon atoms (e.g. methoxy, ethoxy, n-propoxy, n-butoxy, etc.).

The alkyl groups of the dialkylamino moiety preferably are the same or different and have 1 to 7 carbon atoms in a straight or branched chain.

A particularly preferred compound of the formula is the trichloroethyl-1-(p-chloro-benzoyl)-2-methyl-5-methoxy-3-indolyl-acetate, R of the formula being p-chlorophenyl.

The compounds of the recited formula possess useful antiinflammatory and analgesic properties in the treatment of humans (i.e. patients). The pharmacological activity of the above preferably representative of the compounds of the formula is demonstrated in the Examples. The compounds of the formula possess the great advantage of having a very low toxicity.

The pharmaceutical compositions of the present invention may be prepared by methods of pharmaceutical industry known per se by admixing the active ingredient with suitable inert solid or liquid carriers and formulating the same in forms suitable for direct medical use. The pharmaceutical compositions may be provided for use in forms suitable for oral, rectal or parenteral administration. The compositions may be in solid (e.g. tablets, pills, coated pills, capsules, suppositories) semi-solid (e.g. ointments) or liquid form (e.g. solutions, emulsions, or suspensions).

The compositions may contain the usual carriers, such as talc, starch, gelatine, water, polyalkylene glycol, magnesium stearate, calcium carbonate etc. The compositions may also contain usual additives, such as emulsifying, wetting, stabilizing, suspending agents, salts for adjusting osmotic pressure, buffers etc. Further pharmaceutically active substances may also be present in the compositions. Preferred dosage units are the tablets and capsules. These may be prepared by admixing thoroughly the sieved and ground components and filling the homogeneous mixture into capsules. Another preferred dosage form is the suppository intended for rectal administration. These may be prepared by melting the base material of the suppository (e.g. Witepsol W) and homogenously distributing the lump-free powdered active ingredient in the melt and thereupon cooling the mass and filling the same into suppository forms.

The compounds of the first-mentioned formule hereinafter formula (I), may be prepared by; reacting a compound of the formula (II)

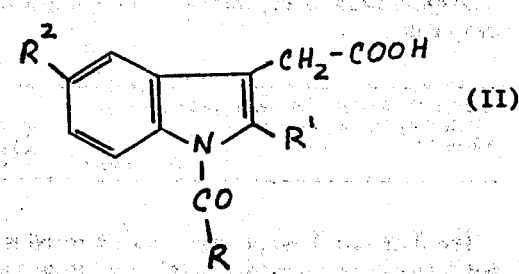

with trichloroethanol or reacting a salt of a compound of the formula (II) formed with an organic base with chloroformic acid trichloroethyl ester and subjecting the mixed anhydride thus obtained to decarboxylation.

The direct esterification may be carried out in the presence of dicyclohexylcarbodiimide or an acid (e.g. p-toluene-sulphonic acid). As a solvent, methylene chloride or another halogenated hydrocarbon may be used.

The reaction between an organic salt of a compound of the formula (II) formed with an organic base and chloroformic acid trichloroethylester is carried out in the presence of an inert solvent (e.g. methylene chloride). The mixed anhydrides thus obtained are then subjected to decarboxylation, generally by heating.

The dosage of the compounds of the formula (I) may vary within wide ranges and depends of the circumstances of the given particular case (e.g. condition of the patient, etc.). The daily dosage of trichloroethyl-1-(p-chlorobenzoyl)-2-methyl-5-methoxy-3-indolyl-acetate may be from about 90 mg. to about 150 mg. in oral administration. The active ingredient content of the compositions may also vary within a wide range. The preferred dosage units (tablets, capsules) may have an active ingredient content of from about 25 mg. to about 50 mg.; particularly preferred is a dosage unit of about 30 mg.

Further details of our invention are to be found in the Examples.

EXAMPLE 1

Capsules having the following compositions are prepared by methods of pharmaceutical industry known per se by admixing the components in the given ratio and filling the thoroughly blended mixture into capsules:

| | |
|---|---|
| Trichloroethyl-1-(p-chloro-benzoyl)-2-methyl-5-methoxy-3-indolyl-acetate (Example 5) | 50 mg. |
| Colloidal silicic acid | 5 mg. |
| Talc | 5 mg. |
| Magnesium-Stearate | 10 mg. |
| Potato starch | 20 mg. |
| Lactose | 20 mg. |

The product is referred to below as HM 957/C.

EXAMPLE 2

Suppositories having the following composition are prepared:

| | |
|---|---|
| Trichloroethyl-1-(p-chloro-benzoyl)-2-methyl-5-methoxy-3-indolyl-acetate | 0.05 g. |
| Witepsol W | 2.08 g. |
| Total weight | 2.13 g. |

The Witepsol W suppository base material is melted and filtered into a mass-forming kettle through a cotton filter. The sieved active ingredient is carefully rubbed with a small portion of the melt cooled to 40°–45° C, whereupon it is added to the content of the mass-forming kettle and stirred until the mass becomes cold. The suppositories are molded at a temperature of 34°–35° C. The suppositories are frozen at a temperature of –5° to –8° C.

EXAMPLE 3

According to the process described in Example 2 suppositories having the following composition are prepared:

| | |
|---|---|
| Trichloroethyl-1-(p-chloro-benzoyl)-2-methyl-5-methoxy-3-indolyl-acetate | 0.10 g. |
| Witepsol W | 2.03 g. |
| Total weight | 2.13 g. |

EXAMPLE 4

36 g. of 1-(p-chlorobenzoyl)-2-methyl-5-methoxy-indol-3-yl-acetic acid are suspended in 400 ml. of methylene chloride, 8 ml. of pyridine and 14 ml. of trichloroethanol are added to the mixture. 21g. of dicyclohexylcarbodiimide are dissolved in 100 ml. of methylene chloride and added to the mixture. The mixture is refluxed for 2 hours, whereafter the precipitated dicyclohexylurea is filtered off. The dichloromethane solution extracted with a 2-N hydrochloric acid solution and with a saturated sodium hydrogen carbonate solution and finally with a sodium chloride solution. After drying on magnesium sulphate the solvent is removed.

The remaining 1-(p-chlorobenzoyl)-2-methyl-5-methoxy-indol-3-yl-acetic acid is recrystallized from 300 ml. of methanol. Melting point: 95°–97° C.

Analysis: Molecular weight 489.19 ($C_{21}H_{17}O_4N Cl_4$)
Calculated: C% 51.58 H% 3.51 N% 2.86 Cl% 29.98.
Found: C% 52.01 H% 3.83 N% 2.80 Cl% 29.5. IR spectra 1.750 (ester -C=O) 1.670 (amide -C=O) 1.140 (ester C-O-C) $R_f$: 0.85 (benzene-ethylacetate 2:1)

EXAMPLE 5

15 g. (10 ml. 01075 moles) of chloroformic acid trichloroethylester are dissolved in 100 ml. of methylene chloride and at –10° C a solution prepared from 18 g. (0.05 moles) of 1-(p-chlorobenzoyl)-2-methyl-5-methoxy-indol-3-yl-acetic acid and 4 ml. of pyridine in 100 ml. of methylene chloride is added. The reaction mixture is stirred for 15 minutes at –10° C, then a solution of 4 ml. of pyridine in 10 ml. of methylene chloride is dropwise added. The temperature is raised to 20°–25° C and the mixture is stirred for a further hour. The solution is extracted with a 2N sulphuric acid solution, with a saturated sodium hydrogen carbonate solution and finally with a saturated sodium chloride solution. The extracted solution is dried on magnesium sulphate and the solvent is removed. The remainder is recrystallized from 180 ml. of methanol. The product obtained is the 1-(p-chlorobenzoyl)-2-methyl-5-methoxy-indol-3-yl-acetic-acid trichloroethyl ester. Mp.: 95–97° C. The results of the tests carried out with 1-(p-chlorobenzoyl)-2-methyl-5-methoxy-indol-3-yl-acetic-acid trichloroethylester are summarized as follows:

I. EXAMINATION OF ANTIINFLAMMATORY EFFECT

1. Kaolin oedema test

The experiments were performed on female rats weighing 110–130 g. divided into groups of 10 animals. The rats were starved for 24 hours prior to the experiment. The test substance was administered orally, the controls obtained the suspending solution without the active ingredient. 1 hour following drug administration the animals were injected s.c. 0.1 ml. of a suspension of 5% kaolin into the foot pad. During the following period the inflammatory reaction is manifested by a swelling of the foot. The diameter of the foot of the treated and control animals was measured 2, 3.5 and 5 hours after s.c. injection of kaolin. The efficiency of the test compound was calculated from the difference of the diameter of the foot in the treated and control animals. Significance was calculated with Student's $t$ test and the effect of the drug was expressed also as per cent.

The results of the experiments are presented in Table 1.

Table 1

| Dose mg./kg. | Effect 2ʰ oedema control | Effect 2ʰ oedema treated | Inhibition % | Inhibition of kaolin oedema Effect 3.5ʰ oedema control | Effect 3.5ʰ oedema treated | Inhibition % | Effect 5ʰ oedema control | Effect 5ʰ oedema treated | Inhibition % |
|---|---|---|---|---|---|---|---|---|---|
| 13.7 | 2.55±0.25 | 2.28±0.50 | 10.6 | 2.90±0.36 | 2.35±0.54 | 19.0 | 3.29±0.34 | 2.56±0.53 | 22.2 |
|  | 2.57±0.17 | 2.39±0.36 | 9.8 | 2.97±0.34 | 2.54±0.53 | 15.1 | 3.26±0.31 | 2.77±0.58 | 15.1 |
| 34 | 2.55±0.25 | 2.27±0.30 | 11.0 | 2.90±0.36 | 2.26±0.30 | 22.1 | 3.29±0.34 | 2.48±0.36 | 24.7 |
|  | 2.87±0.55 | 2.46±0.49 | 13.6 | 3.13±0.70 | 2.47±0.41 | 22.1 | 3.72±0.62 | 2.72±0.62 | 29.9 |
| 51 | 2.31±0.49 | 1.86±0.32 | 19.5 | 2.72±0.43 | 2.05±0.30 | 24.6 | 3.03±0.54 | 2.23±0.28 | 26.4 |

2. Cotton pellet granuloma

The experiments were performed on male rats weighing 140–160 g. In ether anaesthesia a 25±1 g. cotton pellet was placed in each of two subcutaneous pockets in the dorsal region of the animal. The drug was administered orally during a period of 7 days. The controls received a drugfree suspension. The doses seen in the Table were administered in two portions, in the morning and in the afternoon, respectively. On the 8th day the animals were killed and the pellets were dissected. After removal of fat and extraneous tissue, the pellets were dried for 5 hours at 50° C and weighed. The weight of the cotton pellet before implantation was subtracted from the weight of the dried, dissected pellet and drug efficiency was calculated from the obtained difference. Significance was calculated with Student's $t$ test and drug effect was expressed as per cent. The results are shown in Table 2.

Table 2

| Dose mg./kg. | Inhibition of granuloma formation Effect granulom. tissue control | Inhibition of granuloma formation Effect granulom. tissue treated | Inhibition % |
|---|---|---|---|
| 5.5 | 70.4±19.9 | 56.7±11.1 | 19.5 |
| 11 | 70.4±19.9 | 52.0±17.8 | 24.8 |

II. ANALGESIC EFFECT

Male mice weighing 15–18 g. and starved for 16 hours were used for the experiments. The drug was given orally, the control mice obtained a drug-free suspension. After 2 and 4 hours (2ʰ and 4ʰ respectively) the animals were injected with 1days, acetic acid solution (0.1 ml. per mouse) intraperitoneally. Upon the effect of the injection the animals reacted in a few minutes with writhing. The mice were observed for 20 minutes and the number of writhes was counted. Comparison of the number of writhes in the control and the treated animals served as a basis of evaluation of drug effect. Significance was calculated by Student's $t$ test, and efficiency of the drug was expressed as per cent. Each experiment was performed on a group of 12–16 animals. The results are shown in Table 3.

Table 3

| Dose mg./kg. | Analgesic effect 2ʰ Control | 2ʰ treated | Effect % | 4ʰ Control | 4ʰ treated | Effect % |
|---|---|---|---|---|---|---|
|  | 39.4±7.4 | 28.0±9.5 | 29.0 | 39.4±7.9 | 32.1±12.4 | 18.6 |
| 5 |  |  |  |  |  |  |
|  | 51.8±11.6 | 41.1±12.2 | 20.7 | 51.8±11.6 | 41.4±12.6 | 20.1 |
|  | 31.6±5.1 | 10.6±6.4 | 60.8 | 31.6±5.1 | 13.7±10.7 | 56.7 |
| 17 |  |  |  |  |  |  |
|  | 42.0±5.1 | 21.6±11.7 | 51.4 | 42.0±5.1 | 20.6±12.3 | 51.0 |

TOXICITY STUDIES

The experiments were performed on unstarved male mice of 25.30 g. body-weight.

The compound was administered in the form of 1% suspension stabilized with methylcellulose. 10 mice were treated orally administering the drug at a volume of 0.2 ml./10 g. in doses displayed in Table 4. The animals obtained the drug once daily over a period of 7 dyas, i.e. 168 hours. The number of deaths was registered each day. $LD_{50}$ values were calculated according to Litchfield and Wilcoxon. Detailed results are presented in Table 4.

Table 4

| Dose mg/kg | Toxicity on mice by oral administration Number of deaths/number of treated animals Hours following treatment | | | | | | |
|---|---|---|---|---|---|---|---|
|  | 24 | 48 | 72 | 96 | 120 | 144 | 168 |
| 1000 | 0/10 | 0/10 | 0/10 | 0/10 | 0/10 | 0/10 | 0/10 |
| 1500 | 0/10 | 0/10 | 0/10 | 0/10 | 0/10 | 0/10 | 0/10 |
| 2000 | 0/10 | 0/10 | 2/10 | 2/10 | 4/10 | 6/10 | 6/10 |
| 2500 | 0/10 | 1/10 | 1/10 | 3/10 | 4/10 | 6/10 | 7/10 |
| 3000 | 0/10 | 1/10 | 3/10 | 4/10 | 5/10 | 7/10 | 7/10 |

$DL_{50}$: 2150 (1820-2537) mg./kg. p.o. calculated on the basis of deaths occurred during 168 hours.

TESTING OF ULCEROGENIC EFFECT IN RATS

Unstarved rats weighing 160–180 g. were used for the experiment. The animals were divided into groups of 20. The compounds were administered as 1% suspensions stabilized with methylcellulose, by the oral route, at a volume of 0.2 ml./100 g. Treatment was continued for 5 days (1 treatment/day), and was suspended on the 6th and 7th day. On the 8th experimental day the mice were killed by ether overdosage. After laparatomy the stomachs were removed, washed twice in water and thereafter dipped in formaline. An incision was made along the large curvature, then again rinced with water and spread on a PVC plate. The gastric mucosa is evaluated macroscopically by two methods:

1. The ulcer index was calculated. The animals were divided into groups on the ground of the diameter of the largest ulcer and the extent of the changes was scored as follows:

| Diameter mm | 0 | erosion | below 1 | 1 | above 1 |
|---|---|---|---|---|---|
| Number of scores | 0 | 1 | 2 | 3 | 5 |

The number of animals in the individual groups was multiplied by the number of scores and the proucts of multiplications are added and the sum thus obtained is divided by the number of animals.

2. Ulcer counts were calculated. The number of ulcers was counted on each stomach and the total number of ulcers was divided by the number of animals. The small and large intestinates were also examined macroscopically, starting from the pylorus. Changes found in the intestinates were evaluated as "all or naught" and expressed in per cent of the number of animals. Results of the above examinations are presented in Table 5.

Table 5

Examination of ulcus formation after oral treatment in rats

| Dose mg./kg. | Deaths | Number of surviving animals | Ulcer index | Ulcer Number | Per cent of animals exhibiting changes of intest. mucosa |
|---|---|---|---|---|---|
| 27.3 | 1/20 | 19 | 0.58 | 0 | 10.5 |
| 54.7 | 5/20 | 15 | 1.5 | 0.27 | 80 |

III. PHARMACOLOGICAL TEST REPORT

The effects of HM 957/c were compared to that of Indomethacine.

The active agents were administered in equimolar amounts, thus, on the basis of the molecular weights (molecular weight of Indomethacine = 357; molecular weight of HM 957/c = 484) 13.67 mg. of HM 957/c corresponds to 10 mg. of Indomethacine. In the Tables the weight of Indomethacine corresponding to the given dosages of HM 957/c is indicated in brackets.

The antiphlogistic and ulcerogeneous activities of both compounds were tested on rats, while the toxicity tests were performed on mice. The toxicity tests carried out on rats were only of informative nature.

The tests and their results are summarized below:

A. Toxicity

1. Toxicity tests on mice

The tests were carried out on male mice weighing 25 to 30 g., not starved previously. The compounds were administered in a dosage of 0.2 ml. of suspension per 10 g. body weight. The individual dosages indicated in Table 1' were administered to 10 mice each. The given amount of active agent was added in a single dosage, and the animals were dept under observation for 7 days (= 168 hours). The number of deceased animals was recorded daily.

The $LD_{50}$ values were calculated according to the Litchfied-Wilcoxon method, by also taking into account the number of animals perished within 168 hours from the administration. The results of this test are summarized in Table 1'. It appears from a comparison of the $LD_{50}$ values that the medium lethal dosage of HM 957/c is about the tenfold of that of Indomethacine, even when the differences in molecular weights are also taken into consideration.

2. Toxicity tests on rats

The tests were carried out on male rats each weighing 110 to 130 g. 10 animals were treated with the substance in question for 3 months. The active agent was administered orally in a suspension formed with 1% methyl cellulose, in a dosage of 0.2 ml./100 g. body weight. A dosage corresponding to 20 mg./kg. of Indomethacine was added during the first, that corresponding to 40 mg./kg. of Indomethacine during the second, and that corresponding to 60 mg./kg. of Indomethacine during the third month. The animals of the control group received suspending agent only. The animals were treated five times a week, and no treatment was carried out on the sixth and seventh days.

The number of animals dying until the end of the individual treatment stages is given in Table 2'. Owing to the nature of the treatment sufficient data for calculating $LD_{50}$ could not be collected, but when comparing the data of Table 2' with the $LD_{50}$ values calculated for animals treated for a week with an oral dosage of 6.9 mg./kg. of Indomethacine it may be concluded that HM 957/c is far less toxic than Indomethacine not only on mice but also on rats.

During the observation period, the perishment of the animals treated with HM 957/c was the same as for Indomethacine.

B. EXAMINATION OF ULCEROGENEOUS ACTION ON RATS

The tests were carried out on male rats each weighing 160 to 180 g. The animals were not starved prior to treatment. Groups of 20 animals were applied. The compounds to be tested were administered orally in a suspension formed with 1% of methyl cellulose, in a dosage of 0.2 ml./100 g. body weight. The animals were treated for five days, by administering once a day 4 to 8 mg./kg. of Indomethacine, or, respectively, a fivefold dosage of HM 957/c. No treatment was carried out on the sixth and seventh days counted from the start of the test. On the 8th day, the survivals were killed by etheral overnarcosis. The abdominal wall was opened, the stomach was removed, immersed twice into tap water and once into a 5% formaldehyde solution, opened along the greater curvature, rinsed agains as described above, and finally spread out onto a plastic sheet.

Two macroscopic evaluations were carried out on the stomach mucosa:

a. Calculation of ulcer index:

The animals were grouped according to the most serious lesions formed, or the greater ulcer diameter, respectively, and the extent of lesion was scored as indicated below:

| Lesion | 0 | Erosion only | Diameter of ulcer | | |
|---|---|---|---|---|---|
| | | | >1 mm | 1 mm | <1 mm |
| Score | 0 | 1 | 2 | 3 | 5 |

The score numbers obtained for the animals belonging to the same treatment group were added, and the sum was divided by the number of animals.

b. Calculation of ulcer number

The number of ulcers formed on the stomach were counted individually, the obtained counts were added, and the sum was divided by the number of animals.

The small and large intestines of the animals were also examined macroscopically starting from the pylorus. The presence of lesions was recorded, and the percentage occurrence of lesions was calculated for the individual groups.

The results of these tests are summarized in Table 3'. It appears from these data that the extent of perishment caused by HM 957/c in a fivefold dosage with respect to Indomethacine (8 mg./kg.) is 50% lower than that caused by the oral dosage of Indomethacine of 8 mg./kg.

Indomethacine, when added in dosages of 4 and 8 mg./kg. respectively, provoked only slight lesions on the mucous membrane of the stomach, whereas upon the administration of HM 957/c, in a fivefold equivalent, slightly more severe lesions were observed.

The lesions on intestines were far more severe for HM 957/c, added in a fivefold dosage, than that observed for Indomethacine. The requency of occurrence of lesions had doubled upon the administration of HM 957/c.

c. Determination of antiphlogistic activity

1. Rat paw oedema

Inflammatory plantar oedema was provoked by the subplantar injection of 0.1 ml. of 5% kaoline or 0.5% carrageenine on female rats each weighing 110 to 130 g., starved for 24 hours. The dorsoplantar diameter of the test animals was measured with a double-armed instrument prior to the administration of the phlogistic (basic value) and at regular intervals (at 2, 3.5 and 5 hours for kaoline and at 1.5, 3 and 4.5 hours for carrageenine) after the administration of the phlogistic. The substances to be tested were added orally in a suspension containing 1% of methyl cellulose, in a dosage of 0.2 ml./100 g. body weight. The treatment was always carried out 1 hour before the administration of the phlogistic. The animals belonging to the control group received suspending agent only. In order to ensure a uniform hydration grade, 1 ml. of tap water was administered through a stomach tube to the animals simultaneously with the administration of the active agent. During the test period the animals were allowed to consume water ad libitum.

The effect was calculated from the difference of the increase in paw diameter observed in the treated and control groups. The daga are given as percentage efficiacy.

The results of these tests are summarized in Tables 4' and 5'.

The significance level was examined by Student's $t$ test. The significance levels are marked by asterisks; the values of the repeated tests are given separately.

It can be concluded from the data of Tables 4' and 5' that HM 957/c inhibits the phlogistic oedema (provoked with kaoline or carrageenine) in a dosage of about 2.5 times higher than Indomethacine (molar equivalents of the two substances are compared).

2. Cotton granuloma

The tests were carried out on male rats each weighing 140 to 160 g. Two cotton beads, each weighing 23 to 27 mg., were implanted under the dorsal skin of the animals in aether narcosis, under semisterile conditions, along both sides of the vertebral column. The compound under examination was administered twice a day for 7 days in oral dosages of 0.2 ml./100 g. body weight, in a suspension formed with 1% methyl cellulose. On the 8th day the animals were killed by etheral overnarcosis, the granulomes were removed, dried at 50° C for 5 hours, and then weighed. The animals belonging to the control group were treated similarly, but they received suspending agent only. The percentage efficiacy was calculated from the weight differences of the granuloma tissues observed for the treated and control groups. The significance was examined by the $t$ test.

The results are summarized in Table 6.

On the basis of these data the effect of HM 957/c is lower than that of Indomethacine, even when added in a twofold dosage.

D. Analgesic activity
Writhing syndrome

The tests were carried out on male mice each weighing 15 to 18 g., starved for 16 hours prior to treatment. 0.1 ml./10 g. body weight of 1% acetic acid solution was injected intraperitoneally to the animals. The sterile inflammation occurred on the action of acetic acid provoked a characteristic syndrome (writhing). The number of writhings was counted during an observation period of 20 minutes, starting 15 minutes after the administration of acetic acid. The substance to be tested was administered orally as a suspension, in a dosage of 0.1 ml./10 g. body weight 2 to 4 hours before the acetic acid injection. The average number of writhings observed for the treated animals was compared to that observed in the control group, and the percentage inhibition was calculated from the difference. The results are summarized in Table 7.

On the basis of the data it may be concluded that HM 957/c provokes the same effect in a dosage of 2.5 times higher than Indomethacine (the ratio refers to molar equivalents).

As a summary, it can be stated that HM 957/c (the trichloroethyl ester of Indomethacine) is an antiphlogistic with an effect of about 2.5 times weaker than Indomethacine.

Considering the toxicity values, however, the therapeutical width of HM 957 /c is far more favorable than that of Indomethacine.

Table 1'

| | | Toxicity on mice after oral administration | | | | | | |
|---|---|---|---|---|---|---|---|---|
| | | | Perished animals/treated animals | | | | | |
| | Dosage | 24 | 48 | 72 | 96 | 120 | 144 | 168 |
| Compound | mg./kg. | hours after administration | | | | | | |
| Indomethacine | 50 | 0/10 | 0/10 | 0/10 | 0/10 | 0/10 | 0/10 | 0/10 |

Table 1'-continued

| | | Toxicity on mice after oral administration Perished animals/treated animals | | | | | | |
|---|---|---|---|---|---|---|---|---|
| Compound | Dosage mg./kg. | 24 | 48 | 72 | 96 | 120 | 144 | 168 |
| | | hours after administration | | | | | | |
| " | 150 | 0/10 | 0/10 | 0/10 | 2/10 | 4/10 | 6/10 | 6/10 |
| " | 300 | 0/10 | 0/10 | 4/10 | 6/10 | 8/10 | 10/10 | 10/10 |
| " | 500 | 0/10 | 2/10 | 4/10 | 7/10 | 9/10 | 10/10 | 10/10 |
| " | 700 | 1/10 | 5/10 | 5/10 | 7/10 | 9/10 | 9/10 | 10/10 |
| " | 900 | 1/10 | 4/10 | 6/10 | 8/10 | 10/10 | 10/10 | 10/10 |
| HM 957/c | 1367 (1000) | 0/10 | 0/10 | 0/10 | 0/10 | 0/10 | 0/10 | 0/10 |
| " | 2050 (1500) | 0/10 | 0/10 | 0/10 | 0/10 | 0/10 | 0/10 | 1/10 |
| " | 2734 (2000) | 0/10 | 0/10 | 2/10 | 2/10 | 4/10 | 6/10 | 6/10 |
| " | 3417 (2500) | 0/10 | 1/10 | 1/10 | 3/10 | 4/10 | 6/10 | 7/10 |
| " | 4101 (3000) | 0/10 | 1/10 | 3/10 | 4/10 | 5/10 | 7/10 | 7/10 |

The medium lethal dosages calculated by considering the number of animals perished within the observation period of 168 hours are:
Indomethacine: $LD_{50}$ = 140 (110.3 – 177.8) mg/kg, p.o.
HM 957/c: $LD_{50}$ = 2150 (1823 – 2537) mg./kg. p.o. (The equivalent amounts of Indomethacine are: 1572/1333 – 1855/ mg./kg. p.o)

Table 2'

| | Toxicity on rats after oral administration Perished animals/total animals | | | |
|---|---|---|---|---|
| Treatment period | Control | Sum | Treated with × mg./kg. of HM 957/c | Sum |
| 1st month | | 0/10 | 27.3 | 1/10 |
| 2nd month | 1/10 | 1/10 | 54.7 | 1/9 | 2/10 |
| 3rd month | 0/9 | 1/10 | 80.0 | 2/8 | 4/10 |

$LD_{50}$ (Indomethacine) = 6.9 (4.4 to 10.83) mg./kg. p.o. (calculated on the basis of the number of animals perished within one week)

Table 3'

| | Ulcerogeneous effect on rats, after oral administration | | | | | |
|---|---|---|---|---|---|---|
| Compound | Dosage mg./kg. | Perishment | Survivals | Ulcer index | Ulcer number | Animals having lesions on the intestines, % |
| Indomethacine | 4 | 0/20 | 20 | 0.45 | 0.1 | 5 |
| Indomethacine | 8 | 10/20 | 10 | 0.3 | 0 | 40 |
| HM 957/c | 27.3 (20) | 1/20 | 19 | 0.58 | 0 | 10.5 |
| HM 957/c | 54.7 (40) | 5/20 | 15 | 1.5 | 0.27 | 80 |

Table 4'

| | | Inhibition of caoline oedema | | | | | | |
|---|---|---|---|---|---|---|---|---|
| Compound | Dosage mg./kg. p.o. | No. of animals control | treated | 2 hours | | 3.5 hours | | 5 hours | |
| Indomethacine | 10 | 10 | 10 | 14.7 | | 19.5* | | 21.2** | |
| | | 8 | 8 | 19.7*** | (17.2) | 27.6*** | (23.5) | 27.2*** | (24.2) |
| | 25 | 10 | 10 | 33.7*** | | 35.1*** | | 32.1*** | |
| | | 10 | 10 | 32.7*** | (33.2) | 37.1*** | (36.1) | 44.4*** | (38.2) |
| HM 957/c | 13.67 (10) | 8 | 7 | 10.6 | | 19.0* | | 22.2* | |
| | | 10 | 10 | 9.8 | (10.2) | 12.7 | (15.8) | 15.5* | (18.8) |
| | 34.17 (25) | 8 | 8 | 11.0 | | 22.2 | | 24.7 | |
| | | 10 | 10 | 13.6 | (12.0) | 22.1* | (22.1) | 29.9** | (27.3) |
| | 68.35 (50) | 10 | 10 | 21.9** | | 30.2** | | 33.3*** | |
| | 136.7 (100) | 10 | 10 | 26.9** | | 41.1*** | | 37.9*** | |

*p < 0.05
**p < 0.01
***p < 0.001

Table 5'

| | | Inhibition of carrageenine oedema | | | | | | |
|---|---|---|---|---|---|---|---|---|
| Compound | Dosage mg./kg. p.o. | No. of animals control | treated | 1.5 hours | | 3 hours | | 4.5 hours | |
| Indomethacine | 10 | 10 | 10 | 24.1*** | | 32.9*** | | 19.8** | |
| | | 10 | 10 | 20.6** | (22.3) | 28.8*** | (30.8) | 20.9** | (20.3) |
| HM 957/c | 13.67 (10) | 10 | 10 | 9.8 | | 15.8* | | 16.0** | |
| | 34.17 (25) | 10 | 10 | 10.8 | | 18.3*** | | 21.9*** | |
| | 68.35 (50) | 10 | 10 | 14.8 | | 19.9** | | 28.5*** | |

*p <0.05
**p <0.01
***p <0.001

Table 6

| Compound | Daily dosage mg./kg. | Cotton granuloma No. of animals control | treated | Effect % | p |
|---|---|---|---|---|---|
| Indomethacine | 4 | 11 | 11 | 36.0 | 0.001 |
| HM 957/c | 5.5 (4) | 11 | 11 | 19.5 | 0.01 |
|  | 11 (8) | 11 | 10 | 24.8 | 0.001 |

Table 7

| Compound | Dosage mg./kg. p.o. | Writhing syndroma 2 hours | | | | 4 hours | | | |
|---|---|---|---|---|---|---|---|---|---|
| | | No. of animals control | treated | Effect % | average | No. of animals control | treated | Effect % | average |
| Indomethacine | 5 | 15 | 14 | 58.2 | | 15 | 16 | 65.7 | |
| | | | | | 59.6 | | | | 54.7 |
| | | 12 | 12 | 61.1 | | 12 | 12 | 43.7 | |
| | 12.5 | 8 | 8 | 73.6 | | 8 | 8 | 85.8 | |
| | | | | | 70.4 | | | | 77.9 |
| | | 12 | 12 | 67.2 | | 12 | 12 | 70.0 | |
| HM 957/c | 6.8 (5) | 15 | 15 | 29.0 | | 8 | 8 | 18.6 | |
| | | | | | 24.8 | | | | 19.3 |
| | | 12 | 12 | 20.7 | | 12 | 12 | 20.1 | |
| | 17.1 (12.5) | 8 | 8 | 60.8 | | 8 | 8 | 56.7 | |
| | | | | | 56.1 | | | | 53.5 |
| | | 12 | 12 | 51.4 | | 12 | 12 | 51.0 | |

We claim:

1. A method of treating gastric ulcers in a human patient comprising the step of administering orally or rectally an effective amount of an active ingredient in the form of a compound of the formula

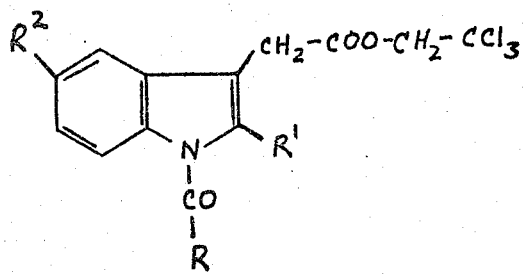

wherein

R is a phenyl chlorophenyl naphthyl, pyrrole, furane, furazole, thiazole, thiadiazole or pyridine group;
$R^1$ is hydrogen or alkyl having 1 to 7 carbon atoms;
$R^2$ is hydrogen, alkyl, having 1 to 7 carbon atoms, alkoxy having 1 to 7 carbon atoms, or dialkylamino having 1 to 7 carbon atoms per alkyl group in admixture with a pharmaceutical carrier.

2. The method defined in claim 1 wherein said compound is trichloroethyl-1-(p-chlorobenzoyl)-2-methyl-5-methoxy-3-idolyl-acetate.

* * * * *